April 6, 1937. P. ECKE Plant Pat. 242
POINSETTIA
Filed June 2, 1936
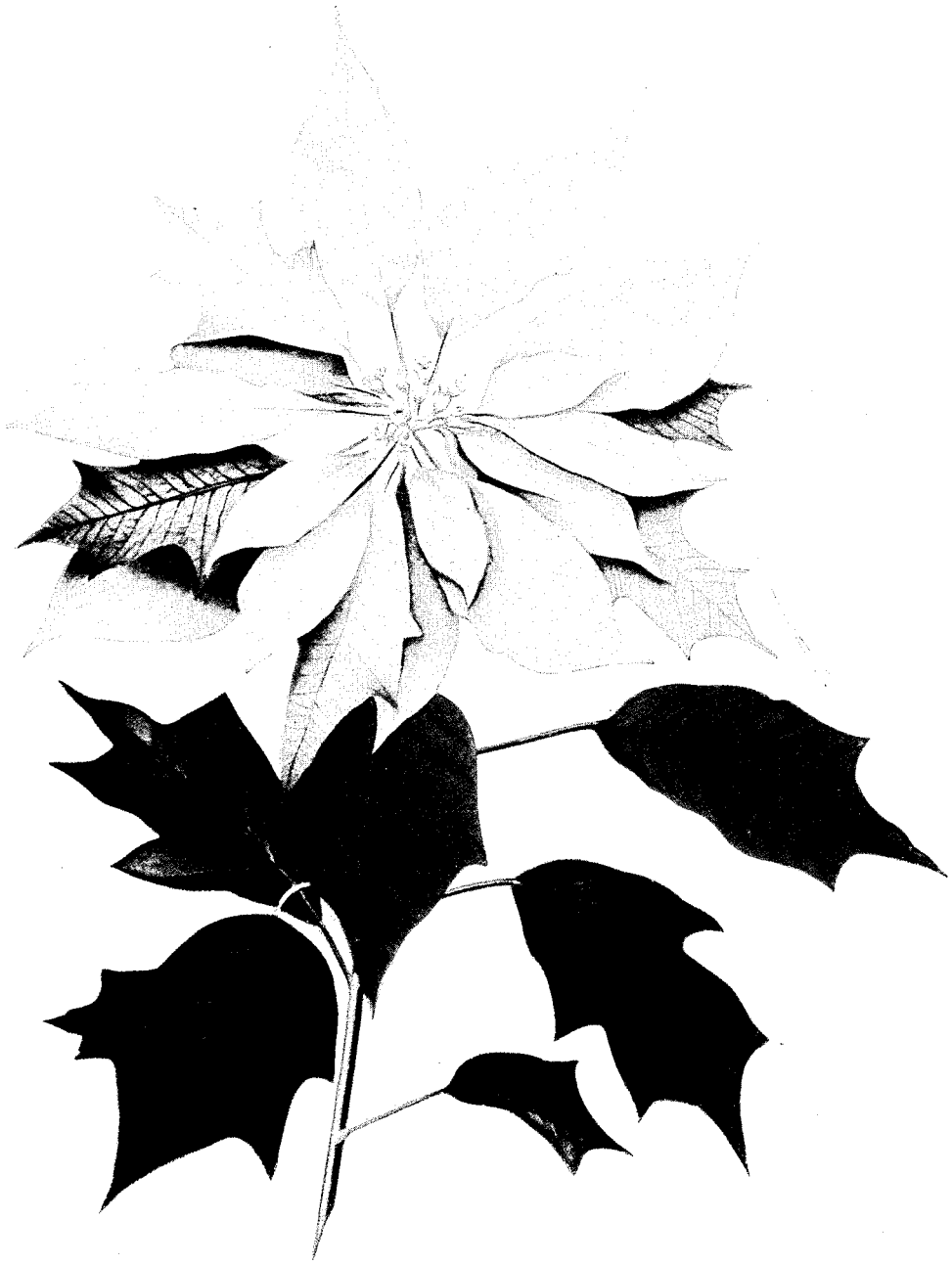
Inventor,
Paul Ecke;
By Robert W. Randle,
Attorney.

Patented Apr. 6, 1937

Plant Pat. 242

UNITED STATES PATENT OFFICE

242

POINSETTIA

Paul Ecke, Encinitas, Calif.

Application June 2, 1936, Serial No. 83,115

1 Claim. (Cl. 47—60)

*Origin*

It is definitely known that the ancestors of the subject of this application originated from a wild free-nature and insignificant shrub, known botanically by the name *"Euphorbia pulcherrima"*, which was found in the wilds of the Republic of Mexico, and exported to the United States by General Joel Robert Poinsett, who at that time was the first United States Minister to Mexico. Some of said plants were received by Robert Buist of Philadelphia, Pa., U. S. A., who improved and further developed them, and named them *"Euphorbia poinsettia"*, in honor of the said discoverer.

After an interval of an unknown number of years, some of the plants, which in the meantime had been improved and domesticated, were taken to the greenhouses of Madsen and Christensen, at the town of Wood Ridge, county of Bergen, State of New Jersey, where they have been reproduced and grown ever since, under the trade name of "Oak Leaf Poinsettia", and perhaps under other specific trade-names.

*Discovery*

Early in the year 1932 a sport of Poinsettia *(Euphorbia pulcherrima)* was discovered in the greenhouses of Madsen and Christensen, Wood-Ridge, New Jersey, and was taken to Encinitas, California, where it has been asexually propagated. It has remained true to type through the propagation of several thousand plants.

*Color Chart*

The colors herein mentioned correspond approximately with those shown and identified by the Robert Ridgway color standard and nomenclature, hereinafter referred to by name, and identified by the color name and page of said color standard.

*Illustration*

The accompanying painting, forming a part of this application, graphically shows the subject in its full maturity, which painting is a face view of the subject, showing it in its normal condition, with its grace and charm of appearance.

*Structure*

The stems are long, stiff, and very strong, and are comparatively small in cross section. Their average length is four feet, with many small branches at the top, usually growing from three knob-like branches. Each branch bears several bracts and a few flowers.

*Petioles*

Extending outwardly from around each of the stems is a plurality of petioles, which are attached to and arranged spirally around their respective stems, with the inner or base portion spanning the interior of its respective stem; with their color similar to that of the stems, but more of a light "Terre Verte" color, shown on Plate XXXIII.

*Leaves*

The leaves are very abundant, and are large and very attractive in appearance. The leaves are long, ovate, and very prominently pinnatifid, the latter being acuminate, similar to that of the leaves of oak trees. The upper side of the leaves are waxy, and are of a "Danube Green" color, similar to that on Plate XXXII; and their under sides are Light Cress Green, shown by Plate XXXI.

After maturity the leaves directly below the bracts (hereinafter explained) down to the third or fourth leaf, will change their color to substantially that of said bracts, but until then they retain their green color. The leaves are arranged alternately on their stems.

*Bracts*

The bracts are similar to the leaves, except that they are much smaller, are lanceolate in contour, do not protrude outwardly so far, and near their maturity they assume a color entirely different therefrom, which is that their upper or face sides are a "Jasper Red", as shown on Plate XIII, and their under sides are a "Pale Salmon color", as shown on Plate XIV.

*Flowers*

A node is formed on the upper end of each peduncle, each of which usually presents three short and comparatively large heavy stem-like knobs, which protrude upward and expansively apart, each of which provides the base for a plurality of short stems, each of which latter carries a flower each of which is of a "Pale Greenish Yellow" color, which is substantially as that shown on Plate V, which prior to maturity is almost white. Each of said flowers usually contains three ovules which, if properly impregnated, will germinate a new Poinsettia. The nine to twelve flowers are very small and are surrounded by the bracts, and they are a "Pale Greenish Yellow", Plate V, which prior to maturity are almost white. Each flower usually develops three seeds, and the seed pods are each about ¼ inch in diameter.

*Appearance*

When looking directly at the center of the bloom, that is at the upper half of the painting, the leaves and bracts form the background of the flowers. Perhaps the most ornamental parts of this Poinsettia are the colored bracts about a cluster of tiny flowers, which make an attractive combination.

*Thorns*

There is nothing of this nature in connection with this plant.

*Dimensions*

The total height of the plant, at maturity, is eight feet, and the greatest lateral dimension is two feet.

*Habits*

Vigorous, but slow in growth; easily cultivated, if properly handled, and persistent and perennial in growth.

*Immunity*

The entire plant seems to be immune from insects, disease, and all other obnoxious and detrimental interference.

*Aroma*

None apparent.

*Variations*

Each of the features mentioned, regarding this plant, is simply a replica of the same in all the others which I have produced, that is to say,—there is very little, if any, difference in the corresponding features. However, in comparison with the same grown in various localities, in different soil, and at various times of the year, in different temperature, or in different greenhouses or in the open, and even by different persons, there may be some slight variations.

*Maintenance*

After being cut, the bloom and the foliage, with ample stem, and even without refrigeration, has the quality of keeping in excellent condition for a period of a week or ten days, depending upon the exterior conditions.

*Planting*

I have found by experience that if a cutting is taken and planted at any time from May until September, that the plant will mature in November, after which it will retain its beauty for two months, after which it will remain dormant for about three months; however the above estimate is subject to variations, depending on the climate and other conditions. It can be grown successfully anywhere in the United States and Canada, in greenhouses kept at the proper temperature, but outdoors only in frost-free sections.

*Comparisons*

Compared with other species of Poinsettia, the differences are principally that this new production presents foliage that is longer and more attractive; it will bloom in a cooler temperature than other known varieties; the bracts are a clearer and more beautiful color; it will produce more perfect bloom; that on a well-grown plant the first three or four leaves below the bracts will turn to a red color, similar to that of the associated bracts; the late cuttings will produce more perfect bloom which are more attractive in every way than any other species of Poinsettia; it is more easy to grow, and produces better results, and retains its beauty for a longer period of time.

*Reproduction*

The reproduction of this new Poinsettia is only by cuttings, which are usually four to five inches long.

Propagation can be successfully continued at Encinitas, California, until early September.

Having now fully shown and described my new Poinsettia, what I claim and desire to secure by Letters Patent of the United States, is—

A new and distinct variety of Poinsettia, substantially as shown and described, characterized especially by the brightness and beauty of colors, its earliness in maturing and persistency in retaining its beauty for a long period after maturity; the changing, after maturity, of some of the leaves from their normally green color to a bright red color; its ability to mature and bloom in a cool temperature; the large size of the plant and its various parts; and the attractive appearance of the entire whole.

PAUL ECKE.